US007413751B2

(12) United States Patent
Devane et al.

(10) Patent No.: US 7,413,751 B2
(45) Date of Patent: Aug. 19, 2008

(54) METHODS OF TREATMENT USING A GASTRIC RETAINED LOSARTAN DOSAGE

(75) Inventors: John Devane, Athlone (IE); K. Iain Cumming, Dublin (IE); Sui Yuen Eddie Hou, Foster City, CA (US); Gloria M. Gusler, Cupertino, CA (US)

(73) Assignee: Depomed, Inc., Menlo Park, CA (US)

( * ) Notice: Subject to any disclaimer, the term of this patent is extended or adjusted under 35 U.S.C. 154(b) by 349 days.

(21) Appl. No.: 10/280,852

(22) Filed: Oct. 25, 2002

(65) Prior Publication Data
US 2003/0158244 A1 Aug. 21, 2003

Related U.S. Application Data

(60) Provisional application No. 60/335,247, filed on Oct. 25, 2001.

(51) Int. Cl.
*A61K 9/24* (2006.01)
*A61K 9/20* (2006.01)
*A61K 9/22* (2006.01)
*A61K 9/14* (2006.01)

(52) U.S. Cl. .................. 424/473; 424/464; 424/468; 424/472; 424/489

(58) Field of Classification Search ................. 424/464, 424/465, 466, 468, 469
See application file for complete search history.

(56) References Cited

U.S. PATENT DOCUMENTS

| | | |
|---|---|---|
| 5,007,790 A | 4/1991 | Shell |
| 5,138,069 A | 8/1992 | Carini et al. |
| 5,264,447 A | 11/1993 | Ohtawa |
| 5,266,583 A | 11/1993 | Ohtawa |
| 5,464,854 A | 11/1995 | DePadova et al. |
| 5,582,837 A | 12/1996 | Shell |
| 5,608,075 A | 3/1997 | Campbell et al. |
| 5,795,904 A | 8/1998 | Cohen et al. |
| 5,824,696 A | 10/1998 | Griswold et al. |
| 5,859,258 A | 1/1999 | Breen et al. |
| 5,872,984 A | 2/1999 | Berglund et al. |
| 5,952,305 A | 9/1999 | Pfeffer et al. |
| 5,972,389 A * | 10/1999 | Shell et al. |
| 5,972,990 A | 10/1999 | Pfeffer et al. |
| 5,985,915 A | 11/1999 | Frangin et al. |
| 6,087,386 A | 7/2000 | Chen et al. |
| 6,093,748 A | 7/2000 | Ahluwalia et al. |
| 6,096,772 A | 8/2000 | Fändriks et al. |
| 6,103,266 A | 8/2000 | Tapolsky et al. |
| 6,110,895 A | 8/2000 | Rodgers et al. |
| 6,127,370 A | 10/2000 | Smith et al. |
| 6,139,847 A | 10/2000 | Chobanian et al. |
| 6,187,340 B1 | 2/2001 | Fukuta et al. |
| 6,191,156 B1 | 2/2001 | Kifor et al. |
| 6,201,002 B1 | 3/2001 | Beere et al. |
| 6,235,766 B1 | 5/2001 | Heitsch et al. |
| 6,248,729 B1 * | 6/2001 | Coniglio et al. |
| 6,340,475 B2 | 1/2002 | Shell et al. |
| 6,451,808 B1 | 9/2002 | Cowles |
| 6,488,962 B1 | 12/2002 | Berner et al. |
| 6,669,955 B2 * | 12/2003 | Chungi et al. |

FOREIGN PATENT DOCUMENTS

| | | |
|---|---|---|
| EP | 1251832 A2 | 10/2002 |
| WO | WO 97/02032 A1 | 1/1997 |
| WO | WO 97/21436 A1 | 6/1997 |
| WO | WO 97/49392 A1 | 12/1997 |
| WO | WO 98/55107 A1 | 12/1998 |
| WO | WO 01/32217 A2 | 5/2001 |
| WO | WO 01/56544 A2 | 9/2001 |
| WO | WO 01/76573 A2 | 10/2001 |
| WO | WO 02/096404 A1 | 12/2002 |

OTHER PUBLICATIONS

U.S. Appl. No. 09/425,491, Shell John W. et al., Not published.
U.S. Appl. No. 10/029,134, Berner et al., Not published.
U.S. Appl. No. 10/014,750, Berner et al., Not published.
U.S. Appl. No. 10/045,816, Berner et al., Not published.
U.S. Appl. No. 10/024,932, Berner et al., Not published.
U.S. Appl. No. 10/066,146, Lim et al., Not published.
U.S. Appl. No. 10/045,823, Shell et al., Not published.
U.S. Appl. No. 10/213,823, Berner et al., Not published.
U.S. Appl. No. 10/235,076, Markey et al., Not published.
U.S. Appl. No. 10/281,284, Berner et al., Not published.
U.S. Appl. No. 10/293,217, Berner et al., Not published.
Andersson et al., "Candesartan Cilexetil vs. Losartan" *J. of Human Hypertension* 12: 419-422 (1998).
Aronow, "Treatment of Congestive Heart Failure in Older Person" *JAGS* 45: 1252-1258 (1997).
Aronow, "The Elite Study: What are its Implications for the Drug Treatment of Heart Failure?" *Drugs & Aging* 12(6): 423-428 (1998).
Awan et al., "Direct Selective Blockade of the Vascular Angiotensin II Receptors in Therapy for Hypertension and Severe Congestive Heart Failure" *American Heart Journal* 131: 177-85 (1996).
Azizi et al., "Pharmacokinetic-Pharmacodynamic Interactions of Candesartan Cilexetil and Losartan" *Journal of Hypertension* 17(4): 561-568 (1999).
Bauer et al., "The Angiotensin II Type 1 Receptor Antagonists" *Arch. Intern Med.* 155: 1361-1368 (1995).
Beevers "Candesartan and Losartan: a Statement From the Editor" *J. of Human Hypertension* 12: 419-422 (1998).
Belz et al., "Inhibition of Angiotensin II Pressor Response and Ex Vivo Angiotensin II Radioligand Binding by Candesartan Cilexetil and Losartan in Healthy Human Volunteers," *J. of Human Hypertension* 11 (Suppl. 2): S45-S47 (1997).
Brunner et al., "Angiotensin II Blockade Compared With Other Pharmacological Methods of Inhibiting the Renin-Angiotensin System," *J. of Hypertension* 11 (Suppl. 3): S53-S58 (1993).
Brunner et al., "Pharmacokinetic II receptor antagonists in normal volunteers," *Kidney International* 49 (Suppl. 55): S24-S29 (1996).
Bunt et al., "Candesartan vs. Losartan" *J. of Human Hypertension* 12: 419-422 (1998).
Burnier et al., "Pharmacokinetic-Pharmacodynamic Relationships of Three Angiotensin II Receptor Antagonists in Normal Volunteers" *Kidney International* 49 (Suppl. 55): S-24-S-29 (1996).

(Continued)

*Primary Examiner*—Humera N Sheikh
(74) *Attorney, Agent, or Firm*—King & Spalding LLP; Judy M Mohr; Paul B Simholi

(57) ABSTRACT

A method of treatment for hypertension and other disease states is described, which comprises the delivery of losartan in a gastric retained dosage form.

20 Claims, 1 Drawing Sheet

OTHER PUBLICATIONS

Burnier et al., "Comparative Antihypertensive Effects of Angiotensin II Receptor Antagonists" *J. Amer. Soc. Of Nephrology* 10: S278-S282 (1999).

Burrell, "A Risk-Benefit Assessment of Losartan Potassium in the Treatment of Hypertension" *Drug Safety* 16(1): 56-65 (1997).

Carr et al., "Losartan: First of a New Class of the Angiotensin Antagonists for the Management of Hypertension" *J. Clin. Pharmacology* 36: 3-12 (1996).

Carson, "Rationale for the Use of Combination Angiotensin-Converting Enzyme Inhibitor Angiotensin II Receptor Blocker Therapy in Heart Failure" *Am. Heart J.* 140: 361-366 (2000).

Christ "Human Plasma Protein Binding of the Angiotensin II Receptor Antagonist Losartan Potassium (Dup 753/ MK 954) and its Pharmacologically Active Metabolite EXP3174" *J. Clin. Pharmacol.* 35:515-520 (1995).

Christ et al., "The Pharmacokinetics and Pharmacodynamics of the Angiotensin II Receptor Antagonist Losartan Potassium (DuP 753/ MK 954) in the Dog" *The J. of Pharm. and Experimental Therapeutics* 268(3): 1199-1205 (1994).

Chung et al., "Angiotensin II Receptor Pharmacology and $AT_1$-receptor Blockers" *Journal of Human Hypertension* 13 (Suppl. 1): S11-S20 (1999).

Coats, "Angiotensin Receptor Blockers—Finally the Evidence is Coming in: IDNT and RENAAL" *Intl. J. of Cardiology* 79: 99-102 (2001).

Csajka et al., "Pharmacokinetic-Pharmacodynamic Profile of Angiotensin II Receptor Antagonists" *Clin. Pharmacokinet.* 32(1): 1-29 (1997).

De Smet et al., "Effect of Multiple Doses of Losartan on the Pharmacokinetics of Single Doses of Digoxin in Healthy Volunteers" *Brit. J. of Clin. Pharmacology* 40:571-575 (1995).

Doba et al., "Drugs, Heart Failure and Quality Of Life: What are we Achieving? What Should we be Trying to Achieve?" *Drugs & Aging* 14(3):153-163 (1999).

Eberhardt et al., "Angiotensin II Receptor Blockade: An Innovative Approach to Cardiovascular Pharmacotherapy" *J. Clin. Pharmacol.* 33: 1023-1038 (1993).

Elliott, "Angiotensin II Antagonists: Efficacy, Duration of Action, Comparison With Other Drugs" *J. of Human Hypertension* 12: 271-274 (1998).

Ellis et al., "A New Class of Antihypertensive Therapy: Angiotensin II Receptor Antagonists" *Pharmacotherapy* 16(5): 849-860 (1996).

Esmail et al., "Losartan as an Alternative to ACE Inhibitors in Patients with Renal Dysfunction" *The Annals of Pharmacotherapy* 32: 1096-1098 (1998).

Fara, J. "Physiological Limitations: Gastric Emptying and Transit of Dosage Forms" in Rate Control in Drug Therapy, L.F. Prescott, et al., Eds., Churchill Livingstone, New York (1985).

Farthing et al., "Simple High-Performance Liquid Chromatography Method for Determination of Losartan and E-3174 Metabolite In Human Plasma, Urine and Dialysate" *J. of Chromatography B* 704: 374-378 (1997).

Foote et al., "New Therapeutic Agents in the Management of Hypertension: Angiotensin II Receptor Antagonists and Renin Inhibitors" *Annals of Pharmacotherapy* 27: 1495-1503 (1994).

Freudenthaler et al., "Dose-Dependent Effect of Angiotensin II on Human Erythropoietin Production" *Eur. J. Physiol.* 439: 838-844 (2000).

Furtek et al., "Simultaneous Determination of a Novel Angiotensin II Receptor Blocking Agent, Losartan, and its Metabolite in Human Plasma and Urine by High-Performance Liquid Chromatography" *J. of Chromatography* 573: 295-301 (1992).

Fyhrquist et al., "Role of Angiotensin II in Blood Pressure Regulation and in the Pathophysiology of Cardiovascular Disorders" *J. of Human Hypertension* 9 (Suppl. 5):S19-S24 (1995).

Gabr et al., "Formulation and Evaluation of Buffered Floating Furosemide Delivery Systems" *STP Pharma Sciences* 10(2): 181-186 (2000).

Gavras et al., "The Angiotensin II Type 1 Receptor Blocker Losartan in Clinical Practice: A Review" *Clin. Therapeutics* 18(6): 1058-1067 (1996).

Gavras et al., "The Antiarrhythmic Potential of Angiotensin II Antagonism: Experience with Losartan" *The Amer. J. of Hypertension* 13: 512-517 (2000).

Goldberg et al., "Effects of Cimetidine on Pharmacokinetics and Pharmacodynamics of Losartan, an $AT_1$-Selective Non-Peptide Angiotensin II Receptor Antagonist" *Eur. J. Clin. Pharmacol.* 49: 115-119 (1995).

Hansson, "The Future Role of Losartan" *J. of Human Hypertension* 9 (Suppl. 5):S55-S58 (1995).

Huskey et al., "N-Glucuronidation Reactions. I. Tetrazole N-Glucuronidation of Selected Angiotensin II Receptor Antagonists in Hepatic Microsomes from Rats, Dogs, Monkeys, and Humans" *The Amer. Soc. For Pharm. And Experimental Therapeutics* 21(5): 792-799 (1992).

Iannuccelli et al., "PVP Solid Dispersions for the Controlled Release of Furosemide from a Floating Multiple-Unit System" *Drug Development and Industrial Pharmacy* 26(6): 595-603 (2000).

Israili, "Clinical Pharmacokinetics of Angiotensin II ($AT_1$) Receptor Blockers in Hypertension" *Journal of Human Hypertension* 14 (Suppl. 1), S73-86 (2000).

Iwasa et al., "Method for the Simultaneous Determination of Losartan and its Major Metabolite, EXP-3174, in Human Plasma by Liquid Chromatography-Electrospray Ionization Tandem Mass Spectrometry" *J. of Chromatography B*, 734: 325-330 (1999).

Ji et al., "Differential Structural Requirements for Specific Binding of Nonpeptide and Peptide Antagonists to the $AT_1$ Angiotensin Receptor" *J. of Biological Chemistry* 269(24): 16533-16536 (1994).

Jiang et al., "Losartan Versus ACE Inhibitors in the Treatment of Hypertension" *The Annals of Pharmacotherapy* 31: 1388-1391 (1997).

Johnston, "Angiotensin Receptor Antagonists: Focus on Losartan" *The Lancet* 346: 1405-07 (1995).

Kang et al., "Angiotensin II Receptor Antagonists: A New Approach to Blockade of the Renin-Angiotensin System" *American Heart Journal* 127: 1388-1401 (1994).

Kaplan, "Angiotensin II Receptor Antagonists in the Treatment of Hypertension" *Amer. Fam. Phy.* 60(4): 1185-1190 (1999).

Karlberg, "Cough and Inhibition of the Renin-Angiotensin System" *J. of Hypertension* 11 (Suppl. 3): S49-S52 (1993).

Kaukonen et al., "Fluconazole but not Itraconzole Decreases the Metabolism of Losartan to E-3174" *Eur. J. Clin. Pharmacol.* 53: 445-449 (1998).

Kazierad et al., "Effect of Fluconazole on the Pharmacokinetics of Eprosartan and Losartan in Healthy Male Volunteers" *Clinical Pharmacology and Therapeutics* 62(4): 417-425 (1997).

Kirk, "Angiotensin-II Receptor Antagonists: Their Place in Therapy" *American Family Physician* 59(11): 3140-3148 (1999).

Lacourciere et al., "Long-Term Comparison of Losartan and Enalapril on Kidney Function in Hypertensive Type 2 Diabetics with Early Nephropathy" *Kidney International* 58:762-769 (2000).

Larsen et al., "Efficient Synthesis of Losartan, a Nonpeptide Angiotensin II Receptor Antagonist" *J. Org. Chem.* 59(21): 6391-6394 (1994).

Lee et al., "Clinical Experience with Angiotensin II Receptor Antagonists" *J. of Human Hypertension* 7 (Suppl. 2): S33-S36 (1993).

Lees et al., "Role Of Angiotensin in the Extravascular System" *J. of Human Hypertension* 7 (Suppl. 2):S7-S12 (1993).

Lo et al., "Pharmacokinetics of Intravenous and Oral Losartan in Patients with Heart Failure" *Journal of Clin. Pharmacol.* 38: 525-532 (1998).

MacFadyen et al., "Angiotensin Receptor Antagonists as a Treatment for Hypertension" *J. of Hypertension* 12(12): 1333-1338 (1994).

McCarthy et al., "Determination of Losartan and its Degradates In COZAAR Tablets by Reversed-Phase High Performance Thin Layer Chromatography" *J. of Pharm. And Biomedical Analysis* 17: 671-677 (1998).

McCrea et al., "Absence of Pharmacokinetic Interaction Between Losartan and Hydrochlorothiazide" *J. Clin Pharmacol.*, 35: 1200-1206 (1995).

McIntyre et al., "Losartan and Orally Active Angiotensin ($AT_1$) Receptor Antagonist: a Review of its Efficacy and Safety in Essential Hypertension" *Pharmacol.* 74(2): 181-194 (1997).

Meadowcroft et al., "The Effects of Fluvastatin, a CYP2C9 Inhibitor on Losartan Pharmacokinetics in Healthy Volunteers" *J. Clin Pharmacol.* 39: 418-424 (1999).

Menon et al., "Development and Evaluation of a Monolithic Floating Dosage Form for Furosemide" *J. Pharmaceutical Sciences*, 83(2): 239-245 (1994).

Mimran et al., "Angiotensin II Receptor and Hypertension" *Clin. And Exper. Hypertension* 21 (5&6): 847-858 (1999).

Miners et al., "Cytochrome PA502C9: An Enzyme of Major Importance in Human Drug Metabolism" *British Journal of Clinical Pharmacology* 45:525-538 (1998).

Moon et al., "Pharmacokinetics of Losartan and its Metabolite, EXP3174, After Intravenous and Oral Administration of Losartan to Rats With Streptozotocin-Induced Diabetes Mellitus" *Research Communications in Molecular Pathology and Pharmacology* 101: (1998).

Munafo et al., "Drug Concentration Response Relationships in Normal Volunteers After Oral Administration of Losartan, an Angiotensin II Receptor Antagonist" *Clin. Pharmacol. Ther.* 51: 513-21 (1992).

Nishikawa et al., "Angiotensin $AT_1$ Receptor Antagonism and Protection Against Cardiovascular End-Organ Damage" *J. of Human Hypertension* 12: 301-309 (1998).

Sever et al., "Discussion 1: New Refinements in the Approach to Hypertension Management" *Journal of Human Hypertension* 13 (Suppl. 1): S33-S34 (1999).

Hall, "Comparison of Losartan and Captopril in ELITE II" *The Lancet* 356: 851-853 (2000).

Ohtawa et al., "Pharmacokinetics And Biochemical Efficacy After Single and Multiple Oral Administration of Losartan, an Orally Active Nonpeptide Angiotensin II Receptor Antagonist, in Humans" *Brit. J. Clinical Pharmacology* 35: 290-297 (1993).

Oparil et al., "Newly Emerging Pharmacologic Differences in Angiotensin II Receptor Blockers" *Amer. J. of Hypertension* 13 (No. 1, Part 2): 18S-24S (2000).

Özdemir et al., "Studies of Floating Dosage Forms of Furosemide: In Vitro and In Vivo Evaluations of Bilayer Tablet Formulations" *Drug Development and Industrial Pharmacy,* 26(8): 857-866 (2000).

Pedro et al., he Pharmacokinetics and Pharmacodynamics of Losartan in Continuous Ambulatory Peritoneal Dialysis *J. Clin. Pharmacol.*40: 389-395 (2000).

Pitt, "ACE Inhibitors in Heart Failure: Prospects and Limitations" *Cardiovascular Drugs* 11: 285-290 (1997).

Pitt et al., "Angiotensin II Receptor Antagonists in Heart Failure: Rationale and Design of the Evaluation of Losartan in the Elderly (ELITE) Trial" *Cardiovascular Drugs and Therapy* 9: 693-700 (1995).

Pitt, "Importance of Angiotensin-Converting Enzyme Inhibitors in Myocardial Infarction and Congestive Heart Failure: Implications for Clinical Practice" *Cardiology* 86 (Suppl. 1): 41-45 (1995).

Puig et al., "Effect of Eprosartan and Losartan on Uric Acid Metabolism in Patients with Essential Hypertension" *J. of Hypertension* 17 (7): 1033-1039 (1999).

Pylypchuk, "ACE Inhibitor Versus Angiotensin II Blocker-Induced Cough And Angioedema" *Annals of Pharmacotherapy* 32: 1060-1066(1998).

Raghavan et al., "A Spectroscopic Investigation of Losartan Polymorphs" *Pharm. Research* 10(6): 900-904(1993).

Regitz-Zagrosek et al., "Effects Of Angiotensin Receptor Antagonists in Heart Failure: Clinical and Experimental Aspects" *Euro. Heart J.* 16 (Suppl. N): 86-91 (1995).

Ribadeneira et al., "Effects of Structural Modifications on the Intestinal Permeability of Angiotensin II Receptor Antagonists and the Correlation of In Vitro, In Situ and In Vivo Absorption" *Pharm. Res.* 13(2): 227-233 (1996).

Ritter et al., "An Improved Method for the Simultaneous Determination of Losartan and its Major Metabolite, EXP3174, in Human Plasma and Urine by High-Performance Liquid Chromatography with Fluorescence Detection" *J. of Pharmaceutical and Biomedical Analysis* 15: 1021-1029 (1997).

Robertson et al., "Agonist-antagonist Interactions at Angiotensin Receptors: Application of a Two-State Receptor Model" *TIPS* 15: 364-369 (1994).

Rush et al., "Theoretical Basis for the Use of Angiotensin II Antagonists in the Treatment of Heart Failure" *J. of Hypertension* 11 (Suppl. 3): S69-S71 (1993).

Sachinidis et al., "EXP3174, A Metabolite of Losartan (MK 954, Dup 753) is More Potent than Losartan in Blocking the Angiotensin II-Induced Responses in Vascular Smooth Muscle Cells" *J. of Hypertension* 11(2): 155-162 (1993).

Sandwall et al., "Lack of Polymorphism of the Conversion of Losartan to its Active Metabolite E-3174 in Extensive and Poor Metabolizers Of Debrisoquine (Cytochrome P450 2D6) And Mephenytoin (Cytochrome P450 2C19)" *European Journal Clinical Pharmacology* 55: 279-283 (1999).

Sasaki et al., "Clinical Pharmacology of Multiple-Dose Losartan, an Angiotensin II Receptor Antagonists, in Patients With Essential Hypertension" *J. Clin. Pharmacol.* 36: 403-408 (1996).

Schaefer et al., "Angiotensin II Receptor Antagonists: the Prototype Losartan" *Annals of Pharmacotherapy* 30(6): 625-36 (1996).

Siegl, "Discovery of Losartan, the First Specific Non-Peptide Angiotensin II Receptor Antagonist" *J. of Hypertension* 11(Suppl. 3):S19-S22 (1993).

Simpson et al., "Losartan, a Review of its Special Focus on Elderly Patients" *Drugs and Aging* 16(3): 227-250 (2000).

Singh et al., "New Classes of Antihypertensive Drugs: Therapeutic Potentials" *Clin. And Exper. Hypertension* 21 (1&2): 137-143 (1999).

Siragy, "Angiotensin II Receptor Blockers: Review of the Binding Characteristics" *Amer. J. of Cardiology* 84(10A): 3S-8S (1999).

Soldner et al., "Active Transport of the Angiotensin-II Antagonist Losartan and its Main Metabolite EXP 3174 Across MDCK-MDR1 and Caco-2 Cell Monolayers" *Brit. Jour. Of Pharmacology* 129(6): 1235-1243 (2000).

Soldner et al., "HPLC Assays to Simultaneously Determine the Angiotensin-$AT_1$ Antagonist Losartan as Well as its Main and Active Metabolite EXP 3174 in Biological Material of Human Rats" *J. of Pharm. And Biomed. Analysis* 16:863-873 (1998).

Soldner et al., "Grapefruit Juice Activates P-Glycoprotein-Mediated Drug Transport" *Pharm. Res.* 16(4): 478-485 (1999).

Song et al., "Pharmacologic, Pharmacokinetic and Therapeutic Differences Among Angiotensin II Receptor Antagonists" *Pharmacotherapy* 20(2): 130-139 (2000).

Stearns et al., "Biotransformation of Losartan to its Active Carboxylic Acid Metabolite in Human Liver Microsomes" *Drug Metabolism and Disposition* 23(2): 207-215 (1995).

Stearns et al., "Short Communication: Synthesis and Identification of a Novel Tetrazole Metabolite of the Angiotensin II Receptor Antagonist DuP 753" *Drug Metabolism and Disposition* 19(6): 1160-1162 (1991).

Stearns et al., "The Metabolism of DuP 753, a Nonpeptide Angiotensin II Receptor Antagonist, by Rat, Monkey, and Human Liver Slices" *The Amer. Soc. For Pharmacology and Experimental Therapeutics* 20(2): 281-287 (1992).

Sweet et al., "How Well Have Studies With Losartan Predicted Responses in Humans?" *J of Hypertension* 11 (Suppl. 3): S63-S67 (1993).

Sweet et al., "Losartan in Heart Failure: Preclinical Experiences and Initial Clinical Outcomes" *Euro. Heart J.* 15 (Suppl.):139-144 (1994).

Tarif et al., "Angiotensin II Receptor Blockade and Progression of Nondiabetic-Mediated Renal Disease" *Kidney International* 52 (Suppl. 63): S67-S70 (1997).

Timmermans et al., "Discovery of Losartan, the First Angiotensin II Receptor Antagonist" *J. of Human Hypertension* 9 (Suppl. 5): S3-S18 (1995).

Timmermans et al., "New Perspectives in Angiotensin System Control" *J. of Human Hypertension* 7 (Suppl. 2):S19-S31 (1993).

Tony Kong et al., "Losartan Does Not Affect the Pharmacokinetics and Pharmacodynamics of Wafarin" *J. Clin. Pharmacol.* 35: 1008-1015 (1995).

Toto "Angiotensin II Subtype 1 Receptor Blockers and Renal Function" *Arch Intern Med*, 161: 1492-1499 (2001).

Triggle, "Angiotensin II Receptor Antagonism: Losartan-Sites and Mechanisms Of Action" *Clinical Therapeutics* 17(6): (1995).

Velasquez, "Angiotensin II Receptor Blockers" *Arch Fam. Med.* 5(6): 351-356 (1996).

Vivian et al., "Slowing the Progression of Renal Disease in Diabetic Patients" *Annals of Pharmacotherapy* 35: 452-463 (2001).

Williamson et al., "Effects of Erythromycin or Rifampin on Losartan Pharmacokinetics In Healthy Volunteers" *Clin. Pharmacology & Therapeutics* 63(3): 316-323 (1998).

Wong et al., "Pharmacology and Pharmacokinetics of a Novel Nonpeptide Angiotensin II Receptor Antagonist-DMP 811" *Clin. And Exper. Hypertension* 17(8): 1233-1256 (1995).

Wong et al., "Nonpeptide Angiotensin II Receptor Antagonists. XI. Pharmacology of EXP3174: an Active Metabolite of DuP 753, an Orally Active Antihypertensive Agent" *J. of Pharmacology and Experimental Therapeutics* 255(1): 211-217 (1990).

Wong et al., "Angiotensin Receptor Antagonists" *Australian Family Physician* 29(7): 653-658 (2000).

Wu et al., "Thermal Analysis and Solution Calorimetry Studies on Losartan Polymorphs" *Pharm. Res.* 10(12): 1793-1795 (1993).

Yanagisawa et al., "Nonpeptide Angiotensin II Receptor Antagonists: Synthesis, Biological Activities, and Structure-Activity Relationships of Imidazole-5-Carboxylic Acids Bearing Alkyl, Alkenyl, and Hydroxyalkyl Substituents at the 4-Position and Their Related Compounds" *J. Med. Chem.* 39(1): 323-338 (1996).

Yun et al., "Oxidation of the Angiotensin II Receptor Antagonist Losartan (DuP 753) in Human Liver Microsomes" *The Amer. Soc. For Pharmacology and Experimental Therapeutics* 23(2): 285-289 (1995).

Zhao et al., "Identification of Losartan Degradates in Stressed Tablets by LC-MS and LC-MS/MS" *J. of Pharm. And Biomed. Anal.* 20:129-136 (1999).

Zusman, "Are There Differences Among Angiotensin Receptor Blockers?" *American J. of Hypertension* 12(12, Part 3):S231-S235 (1999).

* cited by examiner

METHODS OF TREATMENT USING A GASTRIC RETAINED LOSARTAN DOSAGE

This application claims priority under 35 U.S.C. 119(e) to U.S. Provisional Application No. 60/335,247, filed Oct. 25, 2001, the entire content of which is hereby incorporated by reference.

BACKGROUND OF THE INVENTION

1. Technical Field

The present invention relates to the use of losartan in a gastric retained dosage form. More specifically, the invention relates to the use of such dosage form to treat hypertension and other disease states.

2. Background

Losartan was the first orally active angiotensin II receptor antagonist (McIntyre, et al., *Pharmacol. Ther.* 74(2):181-194 (1997); Siegel, *Journal of Hypertension* 11(3):S19-S 22(1993)). At present, losartan is marketed as losartan potassium ($C_{22}H_{22}ClKN_6O$), which is chemically described as 2-butyl-4-chloro-1[p-(o-1H-tetrazol-5-ylphenyl) benzyl] imidazol-5-methanol monopotassium salt. Losartan potassium is administered to treat hypertension and is commercially available in 25 mg, 50 mg and 100 mg tablet dosage forms. Dosage regimens are typically 25 mg to 100 mg either once- or twice-daily.

The effects of losartan potassium are observed at 24 hours for both the 50 mg and the 100 mg dosages, but not for the 25 mg dosage (McIntyre, et al., supra). McIntyre also observes that there is an approximately 30% blockade of the diastolic pressure response to angiotensin II at 24 hours after dosing. Further, the peak:trough blood pressure ratio (5-6 hours after dosing: 24 hours after dosing) was found to be 60% for a 50 mg dosage and 72% for a 100 mg dosage.

Although some researchers have noted that once-daily and twice-daily administrations demonstrate equivalent efficacy, Bauer, et al., *Arch. Intern. Med.* 155:1361-1368 (1995) has indicated that a 50 mg twice daily dosing regimen is more effective than a 100 mg once-daily dosing regimen. Since the blood pressure responses tends to closely follow the plasma levels of the active metabolite of losartan potassium, and the $t_{max}$ and half-life of the active metabolite are 2-4 hours and 6-9 hours (4-5 for Japanese patients tested), respectively (Bauer, et al., supra), the superiority of the bid dosing is expected.

A controlled release formulation of losartan would have the desirable benefit of eliminating the need for bid dosing. It was hypothesized that a gastric retentive controlled release dosage form may improve the absorption of losartan.

These problems are addressed by the instant invention, which provides for the once-daily delivery of losartan by means of a gastric retained dosage form to treat hypertension. A gastric retained dosage form is particularly beneficial for delivery of losartan due to its prolonged transit in the upper gastrointestinal tract and thus not have the problem of reduced bioavailability.

SUMMARY OF THE INVENTION

One aspect of the invention relates to a method of treating hypertension comprising administering a therapeutically effective amount of losartan or a pharmaceutically acceptable salt thereof, in a gastric retained dosage form to a mammal in need of such treatment.

Yet another aspect of the invention relates to a method of treating heart failure comprising administering a therapeutically effective amount of losartan or a pharmaceutically acceptable salt thereof, in a gastric retained dosage form to a mammal in need of such treatment.

Still another aspect of the invention relates to an improved method of administering a therapeutically effective amount of losartan to a patient in need thereof, the improvement comprising administering losartan or a pharmaceutically acceptable salt thereof, in a gastric retained dosage form.

DESCRIPTION OF THE INVENTION

Figure 1:
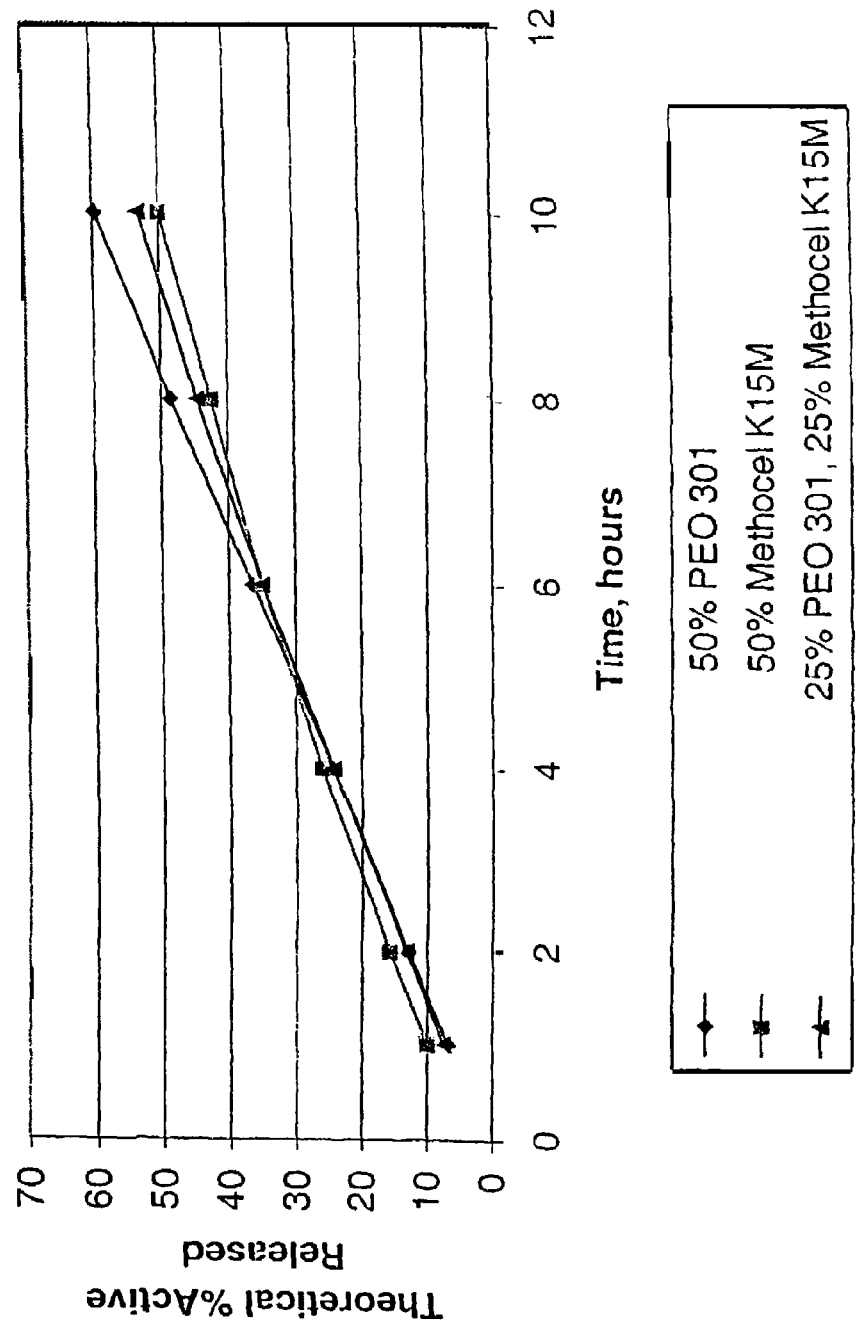
FIG. 1 illustrates in-vitro dissolution of losartan as a function of time.

The invention relates to a method of treating a disease state, such as hypertension, by administering losartan in a once-daily gastric retained dosage form. The gastric retained dosage form is particularly beneficial for delivery of losartan due to its prolonged transit in the upper gastrointestinal tract, which allows the drug to be absorbed adequately. In addition, a gastric retained dosage form increases the $t_{max}$ and allows for a smoother, more prolonged anti-hypertensive effect. Furthermore, a gastric retained losartan dosage form also reduces the $C_{max}$, which may reduce the incidence of losartan's major side effect, dizziness (McIntyre, et al., supra).

Method of Treatment

The instant invention is a method of treating a disease state comprising administering a therapeutically effective amount of losartan, or a pharmaceutically acceptable salt thereof, once-daily in a gastric retained dosage form to a mammal in need of such treatment. As used herein, the term "treating" covers treating the specified disease in a mammal, particularly a human, and includes:

(i) preventing the disease from occurring in a subject which may be predisposed to the disease but has not yet been diagnosed as having it;

(ii) inhibiting the disease, i.e. arresting its development; or (iii) relieving the disease, i.e. causing regression of the disease.

One embodiment of the invention relates to an improved method of administering a therapeutically effective amount of losartan to a patient in need thereof, the improvement comprising administering losartan or a pharmaceutically acceptable salt thereof, in a gastric retained dosage form.

Other embodiments of the invention relate to methods of treating specific disease states comprising administering a therapeutically effective amount of losartan or a pharmaceutically acceptable salt thereof, in a gastric retained dosage form to a mammal in need of such treatment. Such methods find utility in treating numerous disease states that are currently being treated with conventional immediate release formulations of losartan and include, by way of illustration and not limitation, hypertension, congestive heart failure, diabetic nephropathy and myocardial infarction.

The invention also contemplates administering one or more additional therapeutic agents with the losartan treatment. The selection of these additional therapeutic agents will depend upon the specific disease state being treated, and are described in detail below.

Active Ingredient

The active ingredient in the method of the invention is losartan. Losartan is preferably used in the form of a pharmaceutically acceptable salt that retains the biological effectiveness and properties of losartan and is not biologically or otherwise undesirable. As used herein, the term "losartan" is intended to include the agent itself, as well as its pharmaceutically acceptable salts.

Pharmaceutically acceptable salts may be amphoteric and may be present in the form of internal salts. Losartan may form acid addition salts and salts with bases. Exemplary acids that can be used to form such salts include, by way of example and not limitation, mineral acids such as hydrochloric, hydrobromic, sulfuric or phosphoric acid or organic acids such as organic sulfonic acids and organic carboxylic acids. Salts formed with inorganic bases include, for example, the sodium, potassium, lithium, ammonium, calcium, and magnesium salts. Salts derived from organic bases include, for example, the salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethyl aminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, fumarate, maleate, succinate, acetate and oxalate.

A particularly suitable pharmaceutically acceptable salt is losartan potassium ($C_{22}H_{22}ClKN_6O$), which is chemically described as 2-butyl-4-chloro-1[p-(o-1H-tetrazol-5-ylphenyl)benzyl]imidazole-5-methanol monopotassium salt.

Additional Therapeutic Agents

The methods of the invention also contemplate the addition of one or more therapeutic agents with the losartan treatment.

For those embodiments of the invention where the losartan gastric retained dosage form is administered to treat hypertension, such additional therapeutic agents can be selected from the group consisting of diuretics, beta-blockers, angiotensin converting ("ACE") inhibitors, calcium channel blockers, alpha-blockers, alpha-beta blockers, vasodilators, alpha antagonists (centrally acting), and adrenergic neuron blockers; and are preferably selected from the group consisting of diuretics, beta-blockers and calcium channel blockers.

For those embodiments of the invention where the losartan gastric retained dosage form is administered to treat congestive heart failure, such additional therapeutic agents can be selected from the group consisting of diuretics, ACE inhibitors, digoxin, vasodilators (direct vasodilators, calcium channel blockers and nitrates), beta blockers, and statins; and are preferably selected from the group consisting of diuretics, digoxin, direct vasodilators and nitrates.

For those embodiments of the invention where the losartan gastric retained dosage form is administered to treat diabetic nephropathy, such additional therapeutic agents can be diuretics.

For those embodiments of the invention where the losartan gastric retained dosage form is administered to treat myocardial infarction, such additional therapeutic agents can be selected from the group consisting of ACE inhibitors, diuretics, vasodilators, beta blockers, anticoagulants and thrombolytics.

Examples of compounds within each of these classes is set forth below, which is intended to be illustrative and not limiting in any manner Examples of suitable thiazide diuretics include bendroflumethiazide, chlorothiazide, chlorthalidone, hydrochlorothiazide, hydroflumethiazide, methyclothiazide, metolazone, polythiazide, quinethazone and trichlormethiazide; and are preferably selected from the group consisting of hydroclorothiazide and chlorothiazide. Examples of suitable loop diuretics include bumetanide, ethacrynic acid and furosemide. Examples of suitable potassium-sparing diuretics include amiloride, spironolactone and triamterene.

Suitable beta-blockers include propranolol, timolol, and metoprolol.

Examples of suitable ACE inhibitors include captopril, enalapril, lisinopril, quinapril, ramipril, benazepril and fosinopril.

Suitable calcium channel blockers include verapamil, diltiazem, nimodipine, nifedipine, nicardipine, felodipine, isradipine and amlodipine.

Exemplary suitable alpha-blockers include prazosin, terazosin, doxazosin, phenoxybenzamine and phentolamine.

Suitable alpha-beta blockers include labetol.

Examples of suitable vasodilators include, by way of illustration and not limitation, hydralazine, minoxidil, diazoxide and nitroprusside.

Suitable alpha antagonists (centrally acting) include methyldopa, clonidine, guanabenz and guanfacine.

Examples of suitable adrenergic neuron blockers include guantacine, guanethidine, gunadrel, and reserpine.

Dosage

In general, the term "therapeutically effective amount" refers to that amount which is sufficient to effect treatment, when administered to a mammal in need of such treatment. The therapeutically effective amount will vary depending on the subject being treated, the severity of the disease state and the manner of administration, and may be determined routinely by one of ordinary skill in the art.

In particular, for use in the treatment of hypertension or heart failure with a gastric retained dosage form, losartan may be used at doses appropriate for treating hypertension or heart failure with immediate release dosage forms. However, the gastric retained dosage form is designed to provide for bioavailability of losartan at a level greater than or equal to 80% ($\geqq 80\%$) relative to an equal dose of an immediate release dosage form. Typically, the method of the invention will involve administering losartan on a once-daily basis for as long as the condition persists.

An effective amount of losartan per dosage for the treatment of hypertension is typically in the range of about 10-150 mg/dosage, typically about 25-100 mg/dosage, more typically about 50-100 mg/dosage.

An effective amount of losartan per dosage for the treatment of congestive heart failure is typically in the range of about 10-150 mg/dosage, typically about 12.5-100 mg/dosage, more typically about 25-100 mg/dosage.

An effective amount of losartan per dosage for the treatment of diabetic nephropathy is typically in the range of about 10-150 mg/dosage, typically about 12.5-100 mg/dosage, more typically about 25-100 mg/dosage.

An effective amount of losartan per dosage for the treatment of myocardial infarction is typically in the range of about 10-150 mg/dosage, typically about 25-100 mg/dosage, more typically about 25-50 mg/dosage.

Dosage Regimen

The methods of the invention provide a once-daily dose of the losartan gastric retained dosage form. The dosage can be administered at any time, but it is preferred that the dosage is administered at the same approximate time each day for the duration of treatment. In addition, it is preferred that the gastric retained dosage form be taken with food.

Accordingly, in one embodiment of the invention, losartan is administered once-daily in the morning, for example, upon rising or with the morning meal. In another embodiment, losartan is administered once-daily in the evening (e.g., with the evening meal or near bedtime).

In another aspect of the invention, the method of administering a therapeutically effective amount of losartan in a gastric retained dosage form further includes administering one or more additional therapeutic agents.

The additional therapeutic agents can be administered at the same time or at a different time than the administration of losartan, and will depend upon the nature of the disease being treated as well as the agent itself. For example, when the additional agent is a diuretic, a once-daily dose is sufficient and it may be administered at the same time or at a different time than losartan. For purposes of facilitating patient compliance, administration at the same time is preferred.

Dosage Form

There are several drug delivery systems that are suitable for use in delivering losartan in the method of the invention as they are particularly tailored to be gastric-retained dosages, such as the swellable bilayer described by Franz, et al., U.S. Pat. No. 5,232,704; the multi-layer tablet with a band described by Wong, et al., U.S. Pat. No. 6,120,803; the membrane sac and gas generating agent described in Sinnreich, U.S. Pat. No. 4,996,058; the swellable, hydrophilic polymer system described in Shell, et al., U.S. Pat. No. 5,972,389 and Shell, et al., WO 9855107; all of which are incorporated herein by reference.

Of particular interest are gastric retained dosage forms that contain hydrophilic polymers that swell to a size such that it promotes retention of the dosage form in the fed mode. For example, the gastric retained dosage form can contain polymers with a high swelling capacity such as polyethylene oxide, hydroxyethylcellulose and hydroxypropylmethylcellulose. The polymers are preferably of a moderate to high molecular weight ($4 \times 10^3$ to greater than $10^7$) so that the majority of the losartan can be delivered via a diffusional mechanism, but such that eventually the dosage form dissolved in the gastrointestinal tract. In one embodiment of the invention, the dosage form should swell to approximately 115% of its original volume within one hour after administration, and at a later time should swell to a volume that is 150% or more of the original volume. Fillers, binders, lubricants and other additives may also be included in the gastric retained dosage form, such as are well known to those of skill in the art.

A typical dosage form would provide for a drug delivery profile such that losartan both on an in vivo and in vitro basis, is delivered. for at least 5 hours, and typically over a time period of about 6-10 hours. Given the conversion of losartan potassium to its more potent metabolite, the anti-hypertensive effect is ideally sustained more evenly over a 24 hour time period, allowing the once-daily dosing to be effective. In order to provide for sustained delivery, it is preferable that at least 40 wt % of losartan is retained in the dosage form after 1 hour, i.e., no more than 60 wt % of the drug is administered in the first hour. In addition, it may be desired to utilize a dosage form that provides for substantially all of the losartan to be delivered over the intended duration, which is typically about 6-24 hours, where substantially all is taken to mean at least about 85 wt % of the losartan is administered.

In one embodiment of the invention, the gastric retained dosage form of losartan is a capsule dosage form that allows for the extended release of losartan in the stomach and comprises: (a) at least one component that expands on contact with gastric juice and contains an agent capable of releasing carbon dioxide or nitrogen, losartan or a pharmaceutically acceptable salt thereof, (b) at least one hydrophilic membrane in the form of a sachet which contains component (a), expands by inflation, floats on the aqueous phase in the stomach and is permeable to gastric juice and; (c) a capsule dosage form which contains components (a) and (b) and which disintegrates without delay in the stomach under the action of gastric juice. Component (a) may also contain a pharmaceutically acceptable hydrophilic swelling agent such as lower alkyl ethers of cellulose, starches, water-soluble aliphatic or cyclic poly-N-vinylamides, polyvinyl alcohols, polyacrylates, polymethacrylates, polyethylene glycols and mixtures thereof, as well as other materials used in the manufacture of pharmaceutical dosage forms. Further details regarding an example of this type of dosage form can be found in Sinnreich, U.S. Pat. No. 4,996,058.

In another embodiment of the invention, the gastric retained dosage form of losartan is an extended release oral drug dosage form for releasing losartan into the stomach, duodenum and small intestine of a patient, and comprises: a single or a plurality of solid particles consisting of losartan or a pharmaceutically acceptable salt thereof dispersed within a polymer that (i) swells unrestrained dimensionally by imbibing water from gastric fluid to increase the size of the particles to promote gastric retention in the stomach of the patient in which the fed mode has been induced; (ii) gradually the losartan diffuses or the polymer erodes over a time period of hours, where the diffusion or erosion commences upon contact with the gastric fluid; and (iii) releases losartan to the stomach, duodenum and small intestine of the patient, as a result of the diffusion or polymeric erosion at a rate corresponding to the time period. Exemplary polymers include polyethylene oxides, alkyl substituted cellulose materials and combinations thereof, for example, high molecular weight polyethylene oxides and high molecular weight or viscosity hydroxypropylmethylcellulose materials. Further details regarding an example of this type of dosage form can be found in Shell, et al., U.S. Pat. No. 5,972,389 and Shell, et al., WO 9855107.

In yet another embodiment, a bi-layer tablet releases losartan to the upper gastrointestinal tract from an active containing layer, while the other layer is a buoyant or floating layer. Details of this dosage may be found in Franz, et al., U.S. Pat. No. 5,232,704. This dosage form may be surrounded by a band of insoluble material as described by Wong, et al., U.S. Pat. No. 6,120,803.

Another embodiment of the invention uses a gastric retained swellable, sustained-release tablet having a matrix comprised of poly(ethylene oxide) and hydroxypropylmethylcellulose. This dosage form is illustrated in Example 1 and further details may be found in Gusler, et al., "Optimal Polymer Mixtures For Gastric Retentive Tablets," filed on like date herewith and identified as Attorney Docket No. 15662-001700US, the disclosure of which is incorporated herein by reference.

For those embodiments of the invention that include further administering one or more additional therapeutic agents simultaneously with losartan, these agents can either be administered in a gastric retained dosage form that includes losartan or can be administered in a dosage form that is separate from losartan. Exemplary dosage forms are described below.

Dosage Form of Additional Agents

For those embodiments of the invention that include further administering one or more additional therapeutic agents, such dosages can be any suitable formulation as are well known in the art. For those additional agents where controlled release is desirable, the agent may be incorporated in the losartan gastric retained dosage form or be administered in a separate gastric retained or other controlled release formulation dosage form. For those additional agents where immediate release is desirable, the agent may be incorporated in a coating around the losartan gastric retained dosage form, the agent may be simply enclosed in the capsule of the aforementioned losartan gastric retained capsule dosage form, or the agent may be administered in a separate immediate release dosage form.

Typically, dosage forms contain the additional agent (diuretic) in combination with one or more pharmaceutically acceptable ingredients. The carrier may be in the form of a solid, semi-solid or liquid diluent, or a capsule. Usually the amount of active agent is about 0.1-95 wt %, more typically about 1-50 wt %. Actual methods of preparing such dosage forms are known, or will be apparent, to those skilled in this art; for example, see *Remington's Pharmaceutical Sciences*, Mack Publishing Company, Easton, Pa., 18th Edition, 1990. The dosage form to be administered will, in any event, contain a quantity of the additional therapeutic agent(s) in an amount effective to alleviate the symptoms of the subject being treated.

In the preparation of pharmaceutical formulations containing the additional therapeutic agent in the form of dosage units for oral administration the agent may be mixed with solid, powdered ingredients, such as lactose, microcrystalline cellulose, maltodextrin, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets such as chewable and oral disintegrating tablets.

Soft gelatin capsules may be prepared by mixing the active agent and vegetable oil, fat, or other suitable vehicle. Hard gelatin capsules may contain granules of the active agent, alone or in combination with solid powdered ingredients such as lactose, saccharose, sorbitol, mannitol, potato starch, corn starch, amylopectin, cellulose derivatives or gelatin.

Liquid preparations for oral administration may be prepared in the form of syrups or suspensions, e.g. solutions or suspensions containing about 0.2-20 wt % of the active agent and the remainder consisting of sugar or sugar alcohols and a mixture of ethanol, water, glycerol, propylene glycol and polyethylene glycol. If desired, such liquid preparations may contain coloring agents, flavoring agents, saccharin and carboxymethyl cellulose or other thickening agents. Liquid preparations for oral administration may also be prepared in the form of a dry powder to be reconstituted with a suitable solvent prior to use.

When the method of the invention includes administering a diuretic, there are numerous commercially available dosage forms that can be administered, particularly immediate release dosage forms. In addition, other formulations can be readily designed based upon knowledge in the art, and include a coating on the gastric-retained delivery systems described above.

Typical dosage forms of the diuretic suitable for use in the invention include tablets, capsules, oral solutions and oral suspensions. One of skill in the art can readily prepare one of these exemplary formulations or the diuretic can be administered by means of one of the numerous commercially available products, examples of which are provided below.

Commercially available loop diuretics include, for example, Bumex® (bumetanide, Roche Pharmaceuticals), Edecrin® (ethacrynic acid, Merck), Lasix® (furosemide, Hoechst) and Myrosemide (furosemide).

Commercially available potassium-sparing diuretics include, for example, Midamor® (amiloride, Merck), Aldactone® (spironolactone, G. D. Searle) and Dyrenium® (triamterene, Smith Kline).

Commercially available thiazide diuretics include, for example, Naturetin® (bendroflumethiazide, Squibb); Diuril® (chlorothiazide, Merck); Thalitone® (chlorthalidone, Boehringer); Microzide®, HydroDIURIL® and Oretic® (hydrochlorothiazide, Watson, Merck and Abbott, respectively); Saluron® and Diucardin® (hydroflumethiazide, Bristol-Myers and American Home Products, respectively); Enduron® (methyclothiazide, Abbott); Mykrox® and Zaroxolyn® (metolazone, Fisons); Renese® (polythiazide, Pfizer); Hydromox® (quinethazone, American Cyanamid); and Naqua® (trichlormethiazide, Schering).

Although specific examples of suitable diuretic formulations are described above, it is understood that the invention is not limited to those examples as there are numerous other formulations that can be used to deliver the diuretic.

The general methods of the invention are best understood with reference to the following examples which are intended to enable those skilled in the art to more clearly understand and to practice the present invention. These examples are not intended, nor are they to be construed, as limiting the scope of the invention, but are merely illustrative and representative thereof.

EXAMPLE 1

Tablets were manufactured using a dry blend process, and hand-made on a Carver 'Auto C' Press (Fred Carver, Inc., Indiana). The dry blend process consisted of blending all of the ingredients in a container, and compressing into a 600-mg tablet using a 0.6299"×0.3937" Mod Oval die (Natoli Engineering). The parameters for the operation of the Carver Auto 'C' press were as follows: ~2000-2500 lbs. force, 0 second dwell time (the setting on the Carver press), and 100% pump speed.

TABLE 1

| Lot # | Formulation Composition (70 w/w) | | | | |
|---|---|---|---|---|---|
|  | Active | PEO | K15M | LMH | M.St. |
| A | 8.3 | 50.0 | 0.0 | 40.7 | 1 |
| B | 8.3 | 25.0 | 25.0 | 40.7 | 1 |
| C | 8.3 | 0.0 | 50.0 | 40.7 | 1 |

Active = Losartan Potassium
PEO = poly(ethylene oxide), grade PolyOx 301, NF FP grade, manufactured by Union Carbide/Dow Chemical Company
K15M = hydroxypropyl methyl cellulose, grade Methocel K15M, premium, manufactured by Dow Chemical Company
LMH = lactose monohydrate, NF, spray-dried, type Fast Flo 316, manufactured by Foremost Farms
M.St. = magnesium stearate, NF, supplied by Spectrum Chemical Company

EXAMPLE 2

An in vitro cumulative release profile was generated, based upon a theoretical percent active added to the formulations of Example 1. The data are presented in Table 2, and FIG. 1.

TABLE 2

| Time (hours) | Theoretical wt % of Active Released (Dissolution) | | |
|---|---|---|---|
| | A | B | C |
| 1 | 6.9 | 7.4 | 9.9 |
| 2 | 12.8 | 13.4 | 15.9 |
| 4 | 24.3 | 24.3 | 26.1 |
| 6 | 38.4 | 35.0 | 34.8 |
| 8 | 48.6 | 44.5 | 42.5 |
| 10 | 59.8 | 53.4 | 49.9 |

EXAMPLE 3

The following two formulations were manufactured by the dry blend process according to the formulations listed below in Table 3. Losartan potassium was geometrically blended with the remaining excipients by successively blending the losartan potassium with approximately equal quantities of a blend of the remaining excipients until all of the excipients were blended together with the active ingredient. After geometrically blending the losartan potassium, the tablets were compressed at 2500 pounds of force using a 0.3937"×0.6299" modified oval die (Natoli Engineering, St. Charles, Mo.) using a Carver Autopress (Fred Carver, Inc., Wabash, Ind.) with a pharmaceutical die holder. For bi-layer tablets (GR-1) the active layer was placed in the die, tamped lightly, and then filled with the non-active layer. The release of the active component, losartan potassium, is illustrated in Table 4 and is based on the percentage active in the formulation.

TABLE 3

Summary of Prototypes
(50-mg Losartan Potassium per tablet)

| Excipients or Active | GR-1 Active Layer | GR-1 Non-Active Layer | GR-2 |
|---|---|---|---|
| Losartan Potassium | 16.65% | — | 8.29% |
| Hydroxypropyl Methylcellulose (Methocel ® K4M Premium, USP) | — | — | 25.01% |
| Hydroxypropyl Methylcellulose (Methocel ® K15M Premium, USP) | 24.98% | — | — |
| Hydroxypropyl Methylcellulose (Methocel ® K100M Premium, USP) | — | 19.02% | — |
| Polyethylene Oxide (Sentry ® PolyOx ® WSR 301, NF FP) | 24.05% | — | 24.99% |
| (Sentry ® PolyOx ® WSR 303,) NF FP) | — | 64.82% | — |
| Lactose Monohydrate (316 Fast Flo ®, NF) | 33.36% | — | 40.68% |
| Barium Sulfate, USP/NF | — | 15.07% | — |
| Magnesium Stearate, NF/FCC (Mallinckrodt code 2255) | 0.96% | 1.10% | 1.02% |
| Mass (mg) | 300 | 300 | 600 |
| Total Tablet Mass (mg) | 600 | | 600 |

Potassium Losartan was obtained from Gyma Laboratories (Westbury, N.Y.). Methocel® brand hydroxypropyl methylcellulose (also known as hypromellose), USP type 2208, and Sentry® PolyOx® brand polyethylene oxide were obtained from Dow Chemical (Midland, Mich.). FastFlo® 316, NF brand of lactose monohydrate was obtained from Foremost Farms (Baraboo, Wis.). Barium sulfate was supplied by Spectrum Quality Products (New Brunswick, N.J.) and magnesium stearate was obtained from Mallinkrodt (Hazelwood, Mo.). The viscosity of the various types of Methocel® brand hydroxypropyl methylcellulose are 4000 cps, 15,000 cps, and 100,000 cps as a 2% aqueous solution at 20° C. for Methocel® K4M, Methocel® K15M, and Methocel® K100M, respectively. The corresponding number-average molecular weights for Methocel® K4M, Methocel® K15M, and Methocel® K100M are on the order of 80,000, 100,000 and 300,000-350,000, respectively. Sentry® PolyOx® WSR 301, NF FP and Sentry® PolyOx® WSR 303, NF FP have viscosity-average molecular weights of approximately 4,000,000 and 7,000,000, respectively.

TABLE 4

In-vitro Release for Tablets of Example 3

| | % Active Released | |
|---|---|---|
| Time Point | GR-1 | GR-2 |
| 1 hr | 10.69 | 9.39 |
| 2 hr | 25.90 | 20.50 |
| 4 hr | 56.85 | 44.01 |
| 6 hr | 86.97 | 68.09 |
| 8 hr | 95.54 | 88.94 |

EXAMPLE 4

The formulations manufactured in Example 3, with the addition of a radio-opaque string crossed in the center like an "X" in the single layer tablet (GR-2) and in the active layer of the bi-layer tablet (GR-1), were administered to five beagle dogs in a non-randomized pharmacokinetic study with concurrent C-arm fluoroscopy to determine gastric retention. This study used five adult female beagle dogs, weighing approximately 7-9 kg. The dogs were fasted overnight (at least 14 hr) and were then fed a 50-gm meal (a mixture of 50% dry and 50% canned dog food). The immediate release (IR) comparator (Cozaar®, 50 mg tablet, manufactured by Merck & Co.) or one of the GR formulations (GR-1 or GR-2) containing radio-opaque strings was dosed fifteen minutes after the food had been consumed by the dogs. The dosing was done in a non-randomized manner. There was a washout period of at least 6 days between dosing.

The study concurrently determined the pharmacokinetic profile and the gastric retention. The gastric retention was determined by using C-arm fluoroscopy. An image was taken every 30 minutes until either the GR system had emptied from the stomach or it had completely eroded in the stomach. The erosion was determined by the separation of the two strings. Barium sulfate allowed visualization of the swelling layer as well. The pharmacokinetic (PK) analysis was achieved by drawing 3 mL blood samples through venipuncture from either the cephalic or jugular veins. The samples were taken at pre-dosing and at 0.5, 1, 2, 3, 4, 5, 6, 8, 10, 12 and 24 hrs post dosing.

The pharmacokinetic parameters and the gastric retention for are shown in Table 5 below. One dog failed to complete the IR leg. The gastric retention time (GR Time) was the time that the dosage form left the stomach or completely eroded which ever was shorter, as observed using the C-arm fluoroscopy.

TABLE 5

Losartan Potassium Pharmacokinetic Parameters

| | | | | | Relative to the IR | |
|---|---|---|---|---|---|---|
| Pharmacokinetic Parameter | | IR (N = 4) | GR-1 (N = 5) | GR-2 (N = 5) | GR-1 (N = 4) | GR-2 (N = 4) |
| AUC (ng/mL · h) | Mean | 486 | 590 | 461 | 122% | 94% |
| | Std Dev | 133 | 202 | 176 | 29% | 24% |

TABLE 5-continued

Losartan Potassium Pharmacokinetic Parameters

| Pharmacokinetic Parameter | | IR (N = 4) | GR-1 (N = 5) | GR-2 (N = 5) | Relative to the IR | |
|---|---|---|---|---|---|---|
| | | | | | GR-1 (N = 4) | GR-2 (N = 4) |
| $C_{max}$ (ng/mL) | Mean | 224 | 105 | 72 | 48% | 32% |
| | Std Dev | 58.5 | 31.7 | 24.1 | 15% | 8% |
| $t_{max}$ (hr) | Mean | 0.88 | 2.50 | 5.25 | n/a | n/a |
| | Std Dev | 0.25 | 0.58 | 0.50 | n/a | n/a |
| GR Time (hr) | Mean | n/a | 7.6 | 6.8 | n/a | n/a |
| | Std Dev | n/a | 2.5 | 0.5 | n/a | n/a |

As shown in Table 5 above both formulations demonstrated good gastric retention with acceptable bioavailability when compared to the immediate release tablet. The maximum plasma concentration was reduced and the time to maximum plasma was increased as expected for a sustained release product.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating hypertension, comprising: administering a therapeutically effective amount of losartan or a pharmaceutically acceptable salt thereof, in a gastric retentive dosage form to a mammal in need of such treatment, wherein the dosage form consists of a single polymer matrix comprised of losartan or a pharmaceutically acceptable salt thereof and a hydrophilic polymer that swells to a size such that the dosage form is retained in the stomach in the fed mode, and wherein losartan is administered from the dosage form for a period of at least 5 hours and at least 40 wt % of the losartan is retained in the dosage form after 1 hour.

2. The method of claim 1 wherein the dosage form is administered once-daily.

3. The method of claim 2 wherein the dosage form is administered with a meal.

4. The method of claim 1 which further comprises administering one or more therapeutic agents selected from the group consisting of diuretics, beta-blockers, ACE inhibitors, calcium channel blockers, alpha-blockers, alpha-beta blockers, vasodilators, alpha antagonists (centrally acting), and adrenergic neuron blockers.

5. The method of claim 1 wherein the amount of losartan in the dosage form is about 10-150 mg.

6. The method of claim 5 wherein the amount of losartan in the dosage form is about 25-100 mg.

7. The method of claim 6 wherein the amount of losartan in the dosage form is about 50-100 mg.

8. The method of claim 1 wherein the dosage form is an extended release oral drug dosage form for releasing losartan into the stomach, duodenum and small intestine of the mammal.

9. The method of claim 1, wherein the dosage form provides administration of at least 85 wt % of the losartan over a period of about 6-24 hours.

10. The method of claim 1, wherein the polymer is selected from the group consisting of polyethylene oxides, alkyl substituted cellulose materials, and combinations thereof.

11. The method of claim 1 wherein the dosage form is a swellable, sustained-release tablet having a matrix comprised of poly(ethylene oxide) and hydroxypropylmethylcellulose.

12. A method of administering a therapeutically effective amount of losartan to a patient in need thereof, comprising administering losartan or a pharmaceutically acceptable salt thereof, in a gastric retained dosage form, wherein the dosage form consists of a single polymer matrix comprised of losartan or a pharmaceutically acceptable salt thereof and a hydrophilic polymer that swells to a size such that the dosage form is retained in the stomach in the fed mode, and wherein losartan is administered from the dosage form for a period of at least 5 hours and at least 40 wt % of the losartan is retained in the dosage form after 1 hour.

13. The method of claim 12 wherein the dosage form is administered once-daily.

14. The method of claim 13 wherein the dosage form is administered with a meal.

15. The method of claim 12 where the patient is being treated for hypertension.

16. The method of claim 12 wherein the dosage form is an extended release oral drug dosage form for releasing losartan into the stomach, duodenum and small intestine of the mammal.

17. The method of claim 12 wherein the dosage form provides administration of at least 85 wt % of the losartan over a period of about 6-24 hours.

18. The method of claim 12 wherein the polymer is selected from the group consisting of polyethylene oxides, alkyl substituted cellulose materials, and combinations thereof.

19. The method of claim 12 wherein the dosage form is a swellable, sustained-release tablet having a matrix comprised of poly(ethylene oxide) and hydroxypropylmethylcellulose.

20. The method of claim 1 wherein the hydrophilic polymer has a molecular weight of $4 \times 10^3$ to greater than $10^7$.

* * * * *